United States Patent

Biederman

[11] 4,052,792
[45] Oct. 11, 1977

[54] ORTHODONTIC DEVICE

[76] Inventor: William Biederman, 325 Hempstead Ave., Rockville Centre, N.Y. 11570

[21] Appl. No.: 692,314

[22] Filed: June 3, 1976

[51] Int. Cl.² .............................................. A61C 7/00
[52] U.S. Cl. .................................................. 32/14 A
[58] Field of Search ............................. 32/14 R, 14 A

[56] References Cited

U.S. PATENT DOCUMENTS 1,549,739  8/1925  Angle ................................ 32/14 A
3,469,314  9/1969  Pearlman ........................... 32/14 A Primary Examiner—Robert Peshock
Attorney, Agent, or Firm—Stanley J. Yavner

[57] ABSTRACT

An orthodontic appliance with metallic reinforcing members in the form of wires embedded in a plastic base. The metallic reinforcing members include ligatable projections as part of the ligature system for the appliance.

6 Claims, 6 Drawing Figures

ORTHODONTIC DEVICE

This invention relates primarily to a structurally reinforced orthodontic device and more particularly to a device including reinforcement wires serving the dual purpose of reinforcing the device and of forming a part of the ligature system for the device.

For many years now, orthodontists and others skilled in the field of manufacturing, prescribing and applying mechanical devices for treating malformed, misaligned and/or missing teeth have sought to improve orthodontic apparatus for use in their field. Of primary concern has been the aesthetic appearance of orthodontic devices, the strength of such devices and the proper functioning thereof.

Basically, the science of orthodontics includes physiologic, psychologic and mechanical considerations. The mechanical consideration involves the utilization of mechanical appliances for applying force to the teeth over a period of time to insure proper alignment and positioning. Such mechanical appliances are today mostly cemented in place and are formed usually of steel or chrome alloys, precious metals or plastics. It is quite important that such appliances not only perform their physical function, but also provide the means by which such physical functions are performed without adverse effects on the mental and emotional well-being of the patient. Of course, the physical considerations must relate to the elimination of adverse physical results caused by, for instance, breakage of the appliance and the attendant discomfort when the appliances are replaced or adjusted. The phychological consideration involves, most importantly, the aesthetic appeal, or better stated, the lack of an adverse aesthetic result by the wearing of such appliances. This phychological consideration is most important when it is understood that a great many of the orthodontic patients are children of an impressionable age who are judged continuously by their peers.

Accordingly, a primary object of the present invention is to provide a structurally sound mechanical appliance for orthodontic use.

A further primary object of the present invention is to provide an orthodontic appliance or device of improved aesthetic qualities.

A further and more particular object of the present invention is to provide an orthodontic appliance wherein bulk is reduced, or at least not increased, when providing mechanical parts for orthodontic appliances which perform dual functions.

A still further object of the present invention is to combine the aesthetic appeal of plastic orthodontic appliances with the strength for such appliances imparted by the use of metal materials.

These and other objects of the present invention are provided in an orthodontic apparatus which features an orthodontic appliance having a molded plastic base into which is embedded during the molding process, a reinforcing wire. The reinforcing wire is provided at its end portions with ligatable extensions, disposed beyond the plastic base. Other ligatable wires are connected to the ligatable extensions for the purposes of holding in place an arch wire, disposed and movable within an arch wire slot defined by the base. The reinforcing wire is formed in a shape to prevent rotation thereof during use.

Other objects, features and advantages of the present invention will be more fully appreciated by reference to the following, detailed description of the preferred, but nonetheless illustrative, embodiment, when taken in conjunction with the accompanying drawings, wherein.

Figure 1:
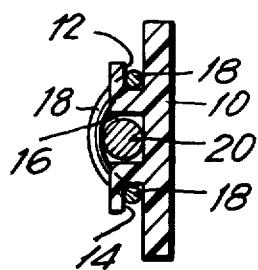
FIG. 1 is a side sectional representation of a common form for an edgewise bracket used presently as part of the prior art for the present invention.

Referring to the drawings, a prior art edgewise bracket is depicted in sectional view in FIG. 1 wherein a plastic base 10 is provided with an upper ligating slot 12, a lower ligating slot 14 and a centrally disposed arch wire slot 16. According to the FIG. 1 prior art form, ligature wire 18 is disposed through the upper and lower ligating slots 12, 14 to hold arch wire 20 in place with respect to the overall orthodontic system being used. The FIG. 1 representation is typical of second generation plastic orthodontic appliances which attempted to replace primarily metal devices with plastic for the sake of appearances. In doing so, designers thereof sacrificed the inherent strength of metal appliances in that upper and lower slots 12, 14 caused a weakness in the overall structure by removing material to provide the ligating slots. Of course, with metal appliances, it was possible to use welding techniques for the purposes of ligating the arch wire and, more importantly, the absence of material from the metal appliances served to weaken the overall structure far less than the weakening illustrated for the plastic appliance. An improvement upon the second generation plastic appliances was attempted by embedding metal members into the plastic appliance. Such metal members were effectively two-dimensional copies of the plastic appliances and served as a flat skeleton to reinforce the plastic. The reinforcing function was performed admirably, but at considerable expense with respect to the use of metal or precious material and with respect to manufacturing costs in terms of placing the metal reinforcing members within the plastic mold. Also, such contrivances served only the function of reinforcement and did not assist in any other way the accomplishment of the orthodontic scheme.

Figure 2:
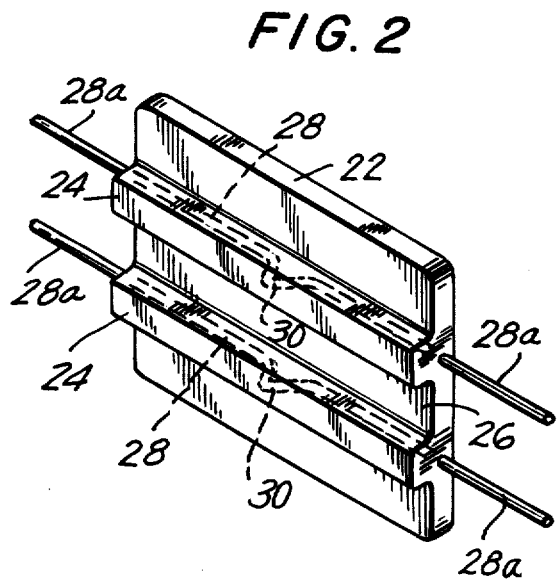
FIG. 2 is an isometric representation of an orthodontic appliance according to the present invention illustrating the improvements thereof over the prior art.

FIG. 2 represents the present invention which features a molded plastic base 22 defining forwardly projecting protrusions 24, which in turn define therebetween an arch wire slot 26. Reinforcing wire 28 is molded in an embedded position with respect to protrusions 24 such that ligatable extensions 28a are disposed beyond base 22 for purposes which will be explained more fully hereinafter. Reinforcing wire 28 is formed in such a way as to avoid rotation during use. For instance, a V-shaped bend 30 is provided to project into protrusions 24 so that rotaton will not occur during use of the appliance.

Figure 3:
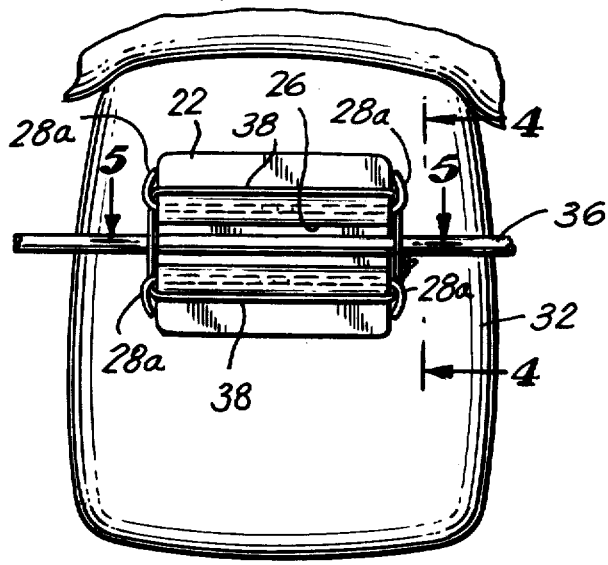
FIG. 3 is a front view representation of an orthodontic appliance according to the present invention, in situ, showing particularly the use of reinforcing wires according to the present invention as part of the ligature system for such appliances.
Figure 4:
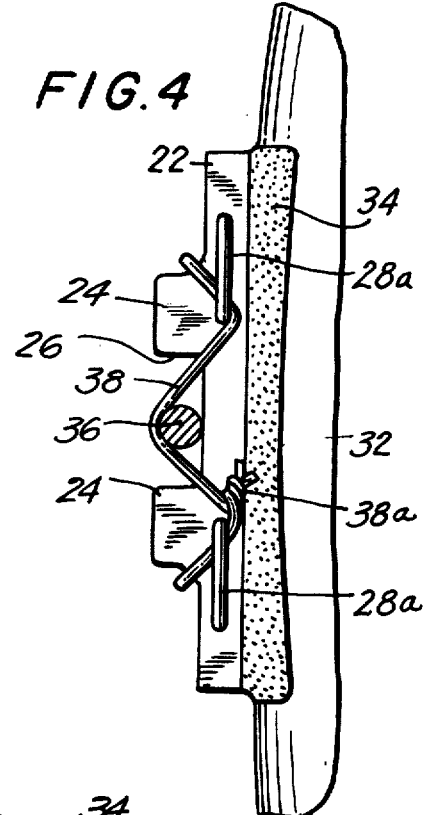
FIG. 4 is a right side view representation of the appliance of FIG. 3, in sectional view taken along the line 4—4 of FIG. 3, and showing particularly the connection of the ligature system with respect to an arch wire useful with the present invention.
Figure 5:
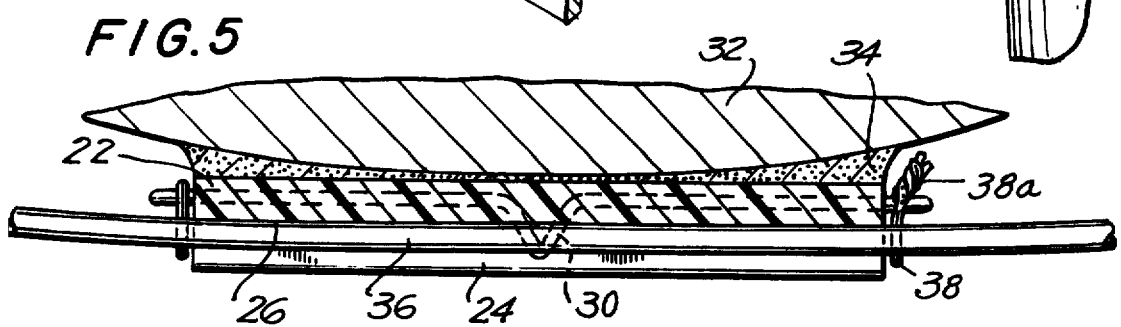
FIG. 5 is a top sectional view of the appliance of FIG. 3, taken along the line 5—5 and showing particularly the form provided for reinforcing wire to prevent rotation.

FIG. 3 shows the appliance of the present invention during use, wherein the appliance is cemented to the labial face of tooth 32 by means of an appropriate adhesive 34 (FIG. 4). Thus, the base 22 of the appliance is fixed with respect to tooth 32 as the appliance performs its physical functions in connection with the wire system. The wire system features an arch wire 36 disposed and laterally movable within arch wire slot 26. Arch wire 36 is held in place from torquing or other undesirable movement by means of a ligature wire system, which includes ligatable extensions 28a of reinforcing wire 28. Such extensions are bent to hold ligature wire 38 in place in a box configuration so that the sides of ligature wire 38 are wrapped over arch wire 36. As can be seen more clearly in FIGS. 4 and 5, one form for securing ligature wire 38 involves knotting such wire at a single point 38a of the ligature system.

Figure 6:
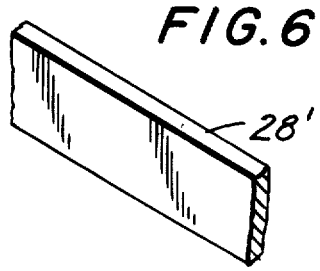
FIG. 6 is an isometric representation of an enlarged segment of reinforcing wire useful in place of the reinforcing wire shown in FIG. 5.

An alternative embodiment of the present invention is illustrated in FIG. 6, which shows a section of reinforcing wire 28' in a rectangular cross-section to prevent rotation during use of the appliance. It may be seen clearly that any non-circular cross section would be satisfactory for the same purpose.

The drawings and this description clearly illustrate the dual function of reinforcing wire 28. Reinforcing wire molded with base 22 provides a strengthening of the appliance in the same way that is provided by reinforcing steel rods in concrete structures common in that field. At the same time, reinforcing wire 28 provides a ligating function wherein ligature wire 28 (or ligature silk or rubber bands) is securely held for performance of its function in holding arch wire 36 from certain movements during the use of the appliance.

Such advantages as are detailed above are provided by the present invention in accordance with the desire of most orthodontists to present other than an adverse appearance for the appliance. It may be seen that most of the wire structure is hidden from view by the plastic of the main body 22 and of the protrusions 24. At the same time, the improved aesthetic value of the appliance is presented by a strengthened structure, unlike full plastic appliances to which the artisans of this field migrated to overcome the look of metal appliances. Furthermore, the improved strength characteristics are provided by the present invention without the use of material-removing slots which have caused breakage and attendant physical discomfort for orthodontic patients. In other words, the less breakage that occurs for the appliances and parts thereof and the less disconnection of parts that occurs, the more comfortable the entire process will be for the various patients.

The present invention has been illustrated herein with reference to an edgewise-type bracket; but it is clear and intended to be clear from this description that the reinforcing structure is useful with other forms of orthodontic appliances.

What is claimed is:

1. An orthodontic appliance having a molded plastic base and defining an elongated arch wire slot for use in connection with orthodontic arch wire comprising a reinforcement opening, reinforcing wire disposed within said opening and having ligatable extensions disposed beyond said base in the direction of the arch wire slot, said reinforcing wire being of a shape to prevent rotation and being held in place by insertion concurrently with molding of said base.

2. The invention according to claim 1 wherein said orthodontic attachment is for use in connection with ligature wire and wherein said ligatable extensions include curved wire beyond said base for engaging said ligature wire to hold said arch wire in place.

3. An orthodontic appliance having a molded plastic base and defining an arch wire slot for use in connection with orthodontic arch wire comprising a reinforcement opening, reinforcing wire disposed within said opening and having ligatable extensions disposed beyond said base, said reinforcing wire being of a shape to prevent rotation and being held in place by insertion concurrently with molding of said base, said plastic base being generally in the form of an edgewise bracket and a forward protrusion extending from said base in the area of said reinforcing wire, said reinforcing wire including a V-shaped bend to prevent rotation, said bend extending into said protrusion.

4. The invention according to claim 1 wherein said reinforcing wire is of a cross-sectional shape other than circular to prevent rotation.

5. The invention according to claim 3 wherein ligature wire is disposed about said protrusion and connected with said ligatable extensions for holding arch wire in place.

6. The invention according to claim 4 wherein said reinforcing wire is of a rectangular cross-sectional shape.

* * * * *